(12) United States Patent
Redfield et al.

(10) Patent No.: US 10,112,029 B2
(45) Date of Patent: Oct. 30, 2018

(54) BONE CONDUCTION APPARATUS AND MULTI-SENSORY BRAIN INTEGRATION METHOD

(71) Applicants: Randall Redfield, Denver, CO (US); Kate O'Brien Minson, Denver, CO (US)

(72) Inventors: Randall Redfield, Denver, CO (US); Kate O'Brien Minson, Denver, CO (US)

(73) Assignee: INTEGRATED LISTENING SYSTEMS, LLC, Denver, CO (US)

( * ) Notice: Subject to any disclaimer, the term of this patent is extended or adjusted under 35 U.S.C. 154(b) by 412 days.

(21) Appl. No.: 13/841,677

(22) Filed: Mar. 15, 2013

(65) Prior Publication Data

US 2013/0225915 A1 Aug. 29, 2013

Related U.S. Application Data

(63) Continuation-in-part of application No. 13/685,390, filed on Nov. 26, 2012, now abandoned, which is a
(Continued)

(51) Int. Cl.
*H04R 23/00* (2006.01)
*A61M 21/00* (2006.01)
(Continued)

(52) U.S. Cl.
CPC .............. *A61M 21/00* (2013.01); *A61F 7/007* (2013.01); *A61M 21/0094* (2013.01);
(Continued)

(58) Field of Classification Search
CPC .................. A61M 2021/0027; H04R 2460/13
(Continued)

(56) References Cited

U.S. PATENT DOCUMENTS

| 4,212,119 A | 7/1980 | Tomatis |
|---|---|---|
| 5,159,640 A | 10/1992 | Bick |

(Continued)

FOREIGN PATENT DOCUMENTS

| CN | 202386359 U | 8/2012 |
|---|---|---|
| KR | 20120003750 A | 1/2012 |
| KR | 20120006665 U | 9/2012 |

OTHER PUBLICATIONS

The Listening Center, "The Tomatis Method", Mar. 21, 2009.*
(Continued)

*Primary Examiner* — Katherine Faley
(74) *Attorney, Agent, or Firm* — Dentons US LLP (57) ABSTRACT

The present disclosure provides a therapeutic method applicable to learning, attention, cognitive and developmental disorders. This method combines auditory, visual and vestibular stimuli into a systematic method which can be customized to address individual learning, attention and processing disorders. This method may be wirelessly implemented in a group setting. A device for providing vestibular and somatosensory stimulation through bone conduction of sound waves to skeletal bones is provided in the form of a pad that is applied to or wrapped around the individual in treatment, which is comfortable in use and may contain particulate filler material capable of providing bone conduction stimulation adjacent to the location of a bone conduction transducer and expand the sound conduction site over a larger area.

7 Claims, 7 Drawing Sheets

Related U.S. Application Data continuation-in-part of application No. 12/456,625, filed on Jun. 19, 2009, now Pat. No. 8,317,734, and a continuation-in-part of application No. 12/804,181, filed on Jul. 15, 2010, now abandoned.

(51) Int. Cl.

| | | |
|---|---|---|
| *A61N 5/06* | (2006.01) | |
| *H04R 1/10* | (2006.01) | |
| *A61N 7/00* | (2006.01) | |
| *A61F 7/00* | (2006.01) | |
| *A61M 21/02* | (2006.01) | |

(52) U.S. Cl.
CPC ............ *A61N 5/0618* (2013.01); *A61N 7/00* (2013.01); *H04R 1/1008* (2013.01); *A61F 2007/0071* (2013.01); *A61F 2007/0093* (2013.01); *A61M 21/02* (2013.01); *A61M 2021/0016* (2013.01); *A61M 2021/0022* (2013.01); *A61M 2021/0027* (2013.01); *A61M 2021/0044* (2013.01); *A61M 2021/0066* (2013.01); *A61M 2205/3368* (2013.01); *A61M 2205/3375* (2013.01); *A61M 2205/3561* (2013.01); *A61M 2205/3569* (2013.01); *A61M 2205/3592* (2013.01); *A61M 2209/088* (2013.01); *A61N 5/0622* (2013.01); *A61N 2005/0647* (2013.01); *H04R 1/1041* (2013.01); *H04R 2420/07* (2013.01); *H04R 2430/01* (2013.01); *H04R 2460/13* (2013.01)

(58) Field of Classification Search
USPC ........................ 381/326, 151; 607/55; 601/47
See application file for complete search history.

(56) References Cited

U.S. PATENT DOCUMENTS

| | | | |
|---|---|---|---|
| 6,248,014 B1 | 6/2001 | Collier | |
| 7,506,927 B1* | 3/2009 | Williams | ............... A61K 9/007 297/180.12 |
| 7,981,064 B2 | 7/2011 | Oser et al. | |
| 8,317,734 B1* | 11/2012 | Redfield | .......................... 601/47 |
| 2003/0079600 A1 | 5/2003 | De Moraes | |
| 2004/0068158 A1 | 4/2004 | Bennett | |
| 2004/0087421 A1* | 5/2004 | Lin | .................... A63B 21/0004 482/146 |
| 2006/0026740 A1* | 2/2006 | Vargas | ................... A41B 11/02 2/239 |
| 2007/0025575 A1* | 2/2007 | Oser et al. | ..................... 381/333 |
| 2007/0041595 A1 | 2/2007 | Carazo et al. | |
| 2007/0053530 A1* | 3/2007 | Ochiai | .................. H04R 5/023 381/151 |
| 2007/0270296 A1* | 11/2007 | Caldicott | ............... A63B 22/14 482/146 |
| 2008/0004677 A1 | 1/2008 | Gay | |
| 2008/0033229 A1 | 2/2008 | Park | |
| 2008/0112581 A1 | 5/2008 | Kim et al. | |
| 2008/0267433 A1 | 10/2008 | Katou et al. | |
| 2008/0306619 A1 | 12/2008 | Cerra et al. | |
| 2009/0010468 A1 | 1/2009 | Oser et al. | |
| 2009/0020521 A1* | 1/2009 | Blaszczykiewicz | .... A61F 7/007 219/529 |
| 2009/0046874 A1* | 2/2009 | Doman | ......................... 381/151 |
| 2009/0060231 A1 | 3/2009 | Buroojy | |
| 2009/0208031 A1 | 8/2009 | Abolfathi | |
| 2009/0304214 A1 | 12/2009 | Xiang et al. | |
| 2010/0087701 A1 | 4/2010 | Berka et al. | |
| 2010/0217349 A1 | 8/2010 | Fahey | |
| 2010/0312042 A1* | 12/2010 | Anderson | ............. A61M 21/02 600/28 |
| 2011/0257468 A1 | 10/2011 | Oser | |
| 2013/0090520 A1* | 4/2013 | Redfield et al. | ................ 600/28 |
| 2013/0225915 A1 | 8/2013 | Redfield et al. | |

OTHER PUBLICATIONS

The Listening Center, Pages "The ADI Method" and "Frequently Asked Questions", Mar. 7, 2005, retrieved from http://www.thelisteningcenter.net.*

Montagnino, "Activities for the Development of Visual Skills", May 9, 2004.*

Boyd-Brewer, "Vibroacoustic Sound Therapy Improves Pain Management and More", May/Jun. 2004, Holistic Nursing Practice, pp. 111-118.*

* cited by examiner

BONE CONDUCTION APPARATUS AND MULTI-SENSORY BRAIN INTEGRATION METHOD

CROSS REFERENCE TO RELATED APPLICATIONS

The present application is a continuation-in-part of U.S. application Ser. No. 13/685,390, filed Nov. 26,2012, which is a continuation-in-part of U.S. application Ser. No. 12/456, 625, filed Jun. 19, 2009 and a continuation-in-part of U.S. application Ser. No. 12/804,181, filed Jul. 15, 2010. Each of Ser. Nos. 13/685,390; 12/456,625; and 12/804,181 is incorporated herein by reference in its entirety.

FIELD OF THE DISCLOSURE

The present disclosure relates generally to a therapeutic method for improving motor function, concentration, visual and auditory processing, cognitive skills (e.g. reasoning, memory, organization, planning and learning) energy level, self-confidence, mood, behavior, anxiousness, and stress level. In at least one embodiment, this method uniquely combines auditory, visual, and vestibular stimuli into a systematic approach which can be customized to address individual learning, attention, and processing disorders. In another embodiment, utilizing a wireless technology system, this method combines the calming effects of bone-conducted sound with the energizing effect of air-conducted music. Such a method, employing a wireless technology system, is a first of its kind in the wellness and preventative health field, employing movement and music to address the proprioceptive, vestibular, and motor aspects of fall risk, as well as reducing the anxiety caused by, for example, the fear of falling. Such method, employing a wireless technology system, has numerous user benefits such as for fall risk reduction, in group wellness/fitness classes, for anxiety reduction, and for general quality of life improvement.

The present disclosure also relates to devices and methods of providing stimulation of the vestibular and somatosensory systems of the human body through bone conduction utilizing one or more transducers to transmit sound frequencies through the skeletal frame.

BACKGROUND OF THE DISCLOSURE

The connection between what is heard and listened to by the ear of a subject and the subject's spoken voice is well recognized. Additionally, it is well recognized that hearing occurs through two distinct pathways: air conduction, which stimulates the cochlear system, and bone conduction (vibration of sound carried by the skeletal frame). Bone conduction delivery of sound occurs when the sound vibration is transmitted to the inner ear through the bones of the skeletal framework. This process stimulates the vestibular/cochlear and somatosensory systems as well as the central nervous system. Stimulating these physiological systems with the low frequencies carried by bone conduction tends to have a relaxing, stabilizing effect; it also influences the ability for spatial equilibrium and balance, as well as the ability to modulate sensory input and to process information. Many devices and methods, including those utilizing bone conduction have been directed toward assisting those with cochlear hearing and vestibular ear difficulties to hear better with an accompanying improvement in speech. Evidence of devices and methods can be found in U.S. Pat. Nos. 3,101, 081, 3,043,913, 4,021,611, 4,212,119, 4,327,252 and 4,615, 680 to Tomatis, U.S. Pat. No. 1,969,559 to Kelly and U.S. Pat. No. 3,101,390 to Maille, all of which are incorporated herein by reference.

In addition to providing the sense of hearing, the vestibular system is the primary organ of equilibrium and plays a major role in the sensation of motion and spatial orientation; it also provides input to the nervous system, adjusting muscle activity, body posture, and stabilizes the eyes during head movements. It is known that vestibular stimulation through air and bone conducted sound can enhance neurological development, and can be used in the treatment of autism, Asperger's, sensory processing disorder, and ADHD. It is widely recognized that the early detection of autism in children is fundamental to effective treatment. However, with very young children, because of the prior art device configurations, effective vestibular stimulation through sound is difficult.

Vestibular stimulation therapy of the prior art has consisted of the delivery of sound through headphones and the delivery of sound through headphones in conjunction with bone conduction delivery through a device attached to the headphones or the person's head. Although effective, the use of the headphones and bone conduction devices attached to a person's head may be uncomfortable and impractical in certain settings. Clearly with infants and small children such headphones and bone conduction devices are not practical; and in any application, such headphones and bone conduction devices can become unintentionally displaced, and therefore ineffective, through the movement of the individual. Further, such headphones and bone conduction devices cannot be applied to provide vestibular stimulation to a fetus in-utero.

Dr. Alfred A. Tomatis postulated and it is well recognized by others that: 1. The voice only contains that which the ear can hear; if you can't hear it, you won't be able to speak it; 2. the ear is like a battery to the brain, with a primary function of converting sound waves to electrical pulses to charge the cortex of the brain; 3. hearing is passive, listening is active and conscious, like the difference between seeing and looking; listening and looking are active focusing processes; 4. the quality of one's listening affects spoken and written language development, alertness, creativity, and the ability to focus; listening also influences communication and shapes social skills, confidence, and self-image; 5. communication begins in utero; an unborn child hears from the 4th month after conception; sound literally helps the brain and nervous system of the fetus to develop. Dr. Tomatis further mapped out and postulated that certain filtered frequencies corresponded to stimulation of certain body and mind properties: frequencies between 0 and 750 Hz corresponded to balance, coordination, motor skills, muscle tone, body awareness, and rhythm; frequencies between 750-3,000 Hz corresponded to memory, concentration, attention, receptive and expressive language; and frequencies greater than 3,000 Hz corresponded to integrating emotion, creativity, and higher cognitive thinking Auditory therapy, including bone conduction, treatment and filtering of music and sounds, and gating are well known in the prior art. Such therapy methods are premised upon the concept of neuroplasticity which holds that throughout the life of the subject new neural connections can be established through stimulation and training Prior to the present disclosure, such auditory therapy has been limited to air conduction and bone conduction listening of music, speech, sounds, and the subject's own spoken voice. No attempt had been made to simultaneously utilize visual tracking stimuli, movement stimuli, and auditory stimuli in such therapy to integrate and refine the cochlear and vestibular signal with that of the other senses.

It is therefore an object of the present disclosure to provide a method of training that systematically integrates auditory, visual, vestibular, and movement sensory inputs.

It is another object of the present disclosure to provide a wirelessly transmitted program of treated music and sounds to wireless bone conduction headphones having a streamlined open ear fit allowing for participation in group exercise/therapy classes, group activities, and socialization. Air conduction signals, if desired, are then outputted via loud speakers to each user in the group setting. Such a program is primarily targeted at seniors who wish to maintain and improve balance during daily activities, but is contemplated as useful in such settings as aerobics classes, sports team training, and schools, etc.

It is another objective of the present disclosure to provide a bone conduction device for stimulation of the vestibular and somatosensory systems that may be utilized with young children and infants including pre-mature infants.

It is another object of the present disclosure to provide a bone conduction device for stimulation of the vestibular and somatosensory systems of a fetus in utero.

It is another object of the present disclosure to provide a bone conduction device for stimulation of the vestibular systems in individuals who receive little or no intrinsic vestibular stimulation as a result of their own limited or lack of movement.

It is another objective of the present disclosure to provide a bone conduction device for stimulation of the vestibular and somatosensory systems that remains effective even when the position of the transducer is displaced by the motion of the individual.

It is another objective of the present disclosure to provide a bone conduction device for stimulation of the vestibular and somatosensory systems that does not require head phones or attachment to the individuals head.

It is another objective of the present disclosure to provide a bone conduction device for stimulation of the vestibular and somatosensory systems that may be comfortably worn and provides stimulation during periods of physical activity and inactivity, including sleep.

It is another objective of the present disclosure to provide a bone conduction device for stimulation of the vestibular and somatosensory systems that includes one or more multi-sensory experiences including but not limited to temperature control, aroma therapy, and/or light therapy.

DESCRIPTION OF THE INVENTION

The present disclosure provides a novel method of training for motor function, sensory processing, and cognitive development. This model systematically integrates auditory, visual, vestibular and movement inputs, developing skills related to self-regulation, motor function, learning, attention, and cognition.

The sequence of the stimuli presented in the method utilized in the present disclosure follows and supports the process of normal development, including movement, sensory processing, learning, language, and higher cognitive function. The inventors herein have postulated and found that this integrated approach, while a continuous process, may be divided into four phases that, in part, mirror the natural development of a healthy child: an organizational phase, an acclimation phase, an activation phase, and an integration phase. The organizational phase is generally the developmental period of early, sub-cortical neurological organization characterized by perception and processing sound with an emphasis on low frequency sound, processing of vestibular and proprioceptive input and gross motor movement. The acclimation phase is generally the developmental period of early childhood where gradual consciousness of sound and early pitch discrimination of frequencies occurs along with basic language acquisition and continued vestibular and proprioceptive development. These occur simultaneously with slow visual tracking, cross-lateral motor development and behavioral, and emotional regulation, including the beginning of impulse control. The activation phase is generally the developmental period marked by the acquisition of higher frequency perception, increased visual and fine motor functions combined with integration of more complex movement and cognitive processing activity, along with increased impulse/behavioral control. The integration phase is the developmental period where there is full integration of all sensory, emotional, and mental inputs marked by the ability to process and integrate multi-sensory input simultaneously with higher cognitive organization and planning.

In the method of the present disclosure, a subject is evaluated to determine the areas of deficiency. The subject is evaluated in connection with a checklist of symptoms indicative of deficiencies of each developmental phase. The checklist includes the areas of sensory motor, auditory, language, social, emotional, and organizational/cognitive functions. Another method of identifying deficiencies in particular phases is to compare "normal" functionality with that of the subject. For example, for pediatric populations this means looking at the subject's developmental age with the typical age for achieving certain developmental landmarks, such as crawling, walking, speaking their first words, and developing a sense of handedness. For adult populations, problems with balance and coordination indicate deficits in the organizational phase; while problems with language and auditory processing indicate deficits in the acclimation phase (e.g. pitch discrimination, auditory processing). Additionally, medical records, particularly indications of ear infections and food allergies, indicate potential resulting deficiencies. Further, LAC, IVA, SCAN-C and BASC-2 assessments are useful in identifying reading, auditory processing and behavior issues indicative of integrative deficiencies of certain phases.

After the areas of difficulty are identified, a therapeutic regimen is created, directed toward remediation of the deficient areas.

The auditory stimulus of the present disclosure is provided by treated music and sounds that are provided through a recording playback device, such as an i-Pod™ or MP3 player, to a pair of headphones. The headphones typically incorporate a bone conduction transducer that transmits sound waves which are carried by the skull to the inner ear; however, the use of the bone conduction transducer is not absolutely necessary in all therapeutic regimens. In therapeutic regimens where the bone conduction transducer is utilized, an amplifier having separate outputs for the headphones and bone conduction transducer is connected to the recording playback device. The amplifier further provides for separate adjustment of the output amplitude directed toward the headphones and separate adjustment of the output amplitude directed toward the bone conduction transducer.

Alternatively or in addition to the previously disclosed embodiment, the treated music and sounds may be provided first to an amplifier/splitter which output a bone conduction signal and an air conduction signal. The bone conduction signal is wirelessly transmitted from a wireless transmitter or from the amplifier/splitter which may include a wireless transmitter. The air conduction signal is connected via conventional wires to one or more room speakers. The wireless transmitter delivers the treated music to a wireless mini-receiver located on a user's body. The wireless mini-receiver is in communication with lightweight streamlined open ear fit bone conduction headphones. In the preferred embodiment, the wireless mini-receiver is physically integrated with the lightweight streamlined open ear fit bone conduction headphones. The mini-receiver, whether integrated or not, provides a user input for adjusting the volume control to the bone conduction transducer in the headphones. The amplifier provides volume control to the room speakers to regulate the delivery of the sound via air waves to one or more users wearing the open ear fit bone conduction headphones. Such a set-up allows a plurality of users to share a group activity, whether that be listening to music, participating in aerobic or non-aerobic exercise, or any other type of social interactive environment, as a group but still benefit from the individual application of a bone conduction signal, synchronized or unsynchronized, with the activity. Additional features of the implementation of this embodiment will be explained in greater detail later in this application.

The stimulation of the visual and movement systems by the present disclosure are provided by activities specifically directed toward the deficits being addressed. The activities are conducted simultaneous to the auditory component (while wearing headphones and listening to processed music). The movement activities fall within five different groups.

The first group of activities consists of breathing, balance and core exercises designed to improve vestibular function, self-regulation, circulation, flexibility, focus, core strength, energy, vitality and reduce fatigue and stress. Although not an exhaustive list, the following described activities are indicative of those from this first group:

Even Breathing: Stand comfortably, head upright, shoulders back and relaxed. Inhale slowly and exhale at same rate. Measure inhales with right hand on right thigh: tap, tap, tap, tap. Measure exhales with left hand on left thigh. 10-20 complete breaths, slow & easy. Adults may count 5-7 beats per inhale, 5-7 per exhale; kids usually 2-4 beats. Harder Alternatives: keep feet together; use balance board. Purpose: self-regulating, calming, posture.

Helicopter Warm up: Stand with feet wide apart, knees slightly bent, arms straight out to sides, palms facing forward. Rotate from the hip to the right, then to the left; back and forth, gradually increasing speed of rotation. Start with ~1 min, gradually increase per ability. Purpose: balance, energy and strength building, aerobic.

Hummingbird Warm up: Stand relaxed, arms straight out to sides, wrists firm, palms down. "Flutter" arms up and down in quick, short motion. After a few sessions of ~30 seconds, gradually increase per ability. This is a deceivingly tiring exercise! Purpose: energy and strength Building.

Cross Kick Warm up: Stand relaxed, hands on hips. Kick right leg to the left crossing midline. Do the same with right leg. Gradually increase the height of the kick, bringing foot higher each session. Keep an even rhythm and make it fun. Alternate: take hands off hips to improve balance. Purpose: hemispheric integration, balance, invigorating warm-up.

Flamingo: Stand on both legs and prepare breathing posture. Raise one leg slightly. Use support (e.g. chair, wall) if needed. Helper times or counts out seconds. Switch legs. Keep record of time, each session try to increase by 10%. Harder Alternatives: combine with even breathing; add memory task. Purpose: building balance, ankle and leg strength.

Balance Board: Place folded blanket or towel under Balance Board (BB). (the thicker, the easier). Stand with knees slightly flexed; try to maintain good posture, head up. Use balance support if needed. 2 minutes eyes open, 30 seconds eyes closed. Use chair or other support, if needed. Purpose: balance.

Wall Push-up: Stand a few feet from wall. Reach hands out and fall towards the wall. With back straight, slowly bend arms, bringing head toward the wall. Push back and drop arms. Reach back out to wall and repeat. Develop rocking rhythm and count out loud. Alternate: add memory-touch chin on 1st push up, touch nose on 2nd, touch forehead on 3rd. Repeat. Start with 5-10, increase each time. Purpose: strengthening, motor planning & coordination.

Arm/Leg Lift: Lay down on back, arms fully extended above head on floor. Lift left leg while raising right leg. Touch as high on leg as possible. Repeat opposite side. Do 10-20 sets, increase set count each session. Purpose: hemispheric integration, motor planning and coordination, flexibility.

Tuff Tummy: Lay down on stomach, arms out front above head. Raise head slightly or rest forehead on floor. Level I: Raise left arm and hold for 10 seconds. Repeat with right arm. Level II: Raise right arm and left leg and count to 10 seconds. Repeat with left arm and right leg. Level III: Raise both arms and legs at same time for 10+ seconds. Purpose: core strength building, motor planning Sunrise Stretch: Inhale as you lift both arms up, reaching to the ceiling. Exhale as you bend down to touch your toes. Repeat 5-10 times, taking slow, big breaths and letting them out with gusto. Increase number of sets with each session and try to get closer to the toes each time. Purpose: invigorating warm-up or relaxing warm-down; strength and flexibility builder.

The second group of activities consists of visual motor activities involving beanbags and a bouncing ball that are designed to improve visual tracking, hand/eye coordination, hemispheric integration and concentration. Although not an exhaustive list, the following described activities are indicative of those from this second group:

Drop & Catch: Drop bean bag or ball from one hand to the other. Switch hands with each drop: left to right, right to left. With each session increase distance of the drop, keep head still, track with eyes only. 20 complete repetitions. Purpose: hemispheric integration, motor planning and coordination.

Toss & Catch: Toss bean bag or ball from one hand to the other. Start low and with confidence toss higher. Reminders: Keep head still, good posture. Make sure eyes are tracking entire arch of bag or ball. Quality is more important than quantity. 20 complete repetitions. Purpose: hemispheric integration, motor planning, visual motor/tracking.

Toss & Catch with partner: Toss bean bag with partner; start tossing straight, then diagonally; Alternative: catch, bring bag or ball around your back to other hand and toss, so a "figure 8" is formed with each complete pattern; 20 complete repetitions. Advanced Alternative:

cross toss 2 bags at same time. Purpose: hemispheric integration, motor planning, visual motor/tracking Floor Bounce & Catch: Bounce ball on floor from left to right, right to left. With partner: play with 1 bounce and then 2 bounces. Advanced: stand 10 feet apart, cross bounce ball left to right, right to left. Place sticky note target for scoring in middle. Listen for a "hit," when ball hits paper. 3-5 minutes. Purpose: hemispheric integration, motor planning, visual motor/tracking Wall/Floor Bounce: Level I: Toss ball against wall so it bounces on floor and returns. Repeat 20-40 times. Easier Alternative: Use larger ball and catch with 2 hands. Harder Alternative: Use small ball and catch with opposite hand. Purpose: hemispheric integration, motor planning and hand-eye coordination.

Wall Bounce and Catch: Toss ball against wall and catch. Repeat 20-40 times. Easier Alternative: use larger ball. Advanced Alternative: use small ball and catch with opposite hand. Purpose: hemispheric integration, motor planning and hand-eye coordination.

Triangle: Toss ball against wall so it hits the wall, then the floor, and returns. Catch with opposite hand; bounce on floor to opposite hand that originated the exercise (forming a triangle). Repeat circuit 5 times and switch to other side. Purpose: hemispheric integration, motor planning and hand-eye coordination.

Under & Twirl: Stand with back to wall, 5-10 feet from wall. Bounce ball under and between legs so it hits the ground and bounces off wall. Twirl around and catch. Repeat 10 times. Easier Alternative: use larger ball, catch with both hands. Harder Alternative: use small ball and catch with opposite hand. Purpose: motor planning, balance, coordination.

The third group of activities consists of visual motor activities involving a hanging ball that are designed to improve visual tracking, hand/eye coordination, hemispheric integration and concentration. Although not an exhaustive list, the following described activities are indicative of those from this third group:

Straight Line Tap: With partner or alone, tap ball in a straight, controlled line, alternate hands. 20-40 complete circuits Maintain good posture, try to keep head still and let your eyes do the tracking. Alternative: alternate palm with back of hand. Purpose: visual motor exercise, hemispheric integration, concentration.

Arc Swing Tap: Using hands (or ping pong paddle to make easier), tap one way then tap in opposite direction with other hand. This is harder than it appears. Keep trying to create a smooth, round arc. Alternative: Stare straight ahead and track with peripheral only. 20-40× Purpose: visual motor exercise, hemispheric integration, concentration.

Straight Head Tap: Tap ball with forehead gently in straight line. Keep line straight in a slow, controlled movement. Warning: be careful not to hit plastic piece above ball. Be patient as this game takes a little practice! Purpose: visual motor exercise, hemispheric integration, motor planning Surprise: User stands under ball plum line, helper arcs ball from behind w/o saying which way it's coming from. User has to catch the ball as it circles around. Win points catching w/o touching string, lose points if miss ball. Advanced alternative: Try to catch ball before it reaches "12:00". Purpose: fast visual tracking, motor planning, concentration.

Dodge Ball: User stands under ball plum line; user or helper starts a broad arc. User must count the revolutions, avoiding contact with ball. Moving head and body is ok, but must not move feet. Winner avoids the ball for the most revolutions. Advanced alternative: cover the eye opposite oncoming ball. Purpose: balance, body awareness and control, eye tracking.

Scan Ball: User stands (or kneels) with ball at eye level. Helper swings ball in straight line "perpendicular" to user so user eye movements are scanning left and right. Start 3 feet back, count 10 swings. Repeat at 2 feet back and again at 1 foot back. Keep head still and count each swing. This is tiring, be careful not to overdo it! Purpose: lateral eye tracking.

Sparring: Using a careful, gentle "punch," alternate left and right as if sparring with the ball. The smaller the fist, the more difficult this is. Little ones might find a slap easier. Games: count the number of consecutive punches, stop as soon as you miss. Highest count wins. Advanced: add footwork, left foot forward for right hand, right foot for left hand. Purpose: motor planning, hand-eye coordination, hemispheric integration.

Bowling: Use plastic bottles as pins. Lengthen string so ball is close to the floor. Score points for hitting, or missing, pins. Create your own games. This is a fun "reward" game to end a session on! Purpose: eye tracking, motor planning.

The fourth group of activities consists of digital dexterity activities designed to improve digital dexterity, fine motor control, aerobic capacity and hemispheric integration. Although not an exhaustive list, the following described activities are indicative of those from this forth group:

Standing Cross-Crawl: Standing, lift left knee and slap with right hand, lift right knee and slap with left hand. Repeat counting to 20. Alternative: count to 100 by 5's, or in another language. Advanced Alternative: Use elbows instead of hands. Purpose: hemispheric integration, coordination, concentration, motor planning From the Brain Gym®, used with permission.

Cross-Crunch: Lay face up on floor with knees bent and feet flat on floor. Place fingertips, unclasped behind head. Do sit-up, bending left knee in to touch right elbow. Repeat on opposite side. Continue alternating elbow to knee rhythmically for 5-10 sit-ups. Increase 10% each session.

Lazy 8: Use either one's own thumb or a dowel with a ribbon tied to the end, to make a large FIG. 8 out in front of body. Do with left hand for 5 full 8's, repeat with right hand. Repeat 5× with right eye covered, and 5× again with left eye covered. Make sure eyes are tracking entire 8. From the Brain Gym®, used with permission.

Crazy Count: Starting with right hand, touch thumb and index finger, then thumb and middle finger, continuing down to the pinky. Repeat 5 times. Repeat 5 times with eyes closed. Repeat with opposite hand 5×. Repeat with eyes closed 5×. Repeat with both hands 5×. Repeat with eyes closed 5×. Advanced Alternate: Touch forefinger, then ring finger, then middle finger, then pinky. Do for 1-2 minutes. Purpose: digit individuation and fine motor control.

Thumb Game: Make first with thumbs inside. Open first and close with thumb on top of fist. The progression is to do the opposite on each hand-left hand thumb in, right hand thumb out. Purpose: fine motor dexterity, digit individuation.

Parallel Skiing: Make a line on floor using fabric or marker. Stand with feet parallel to line and jump over line 10 times. Beginner: jump in place. Advanced: add forward movement. Purpose: hemispheric integration, aerobic, gross motor control, strengthening.

Scissor Legs: Make a line on the floor using tape, chalk or fabric, place one foot on either side of the line. Jump and move feet to opposite sides of the line. Do 10×, catch breath and repeat. Purpose: hemispheric integration, aerobic, gross motor control, strengthening.

Jumping Jacks: Stand with good posture and legs together. As you jump, legs go out and hands go up to touch above head. Count out loud. 10-20×, increase 10% each time. Advanced alternative: counting by even or odd numbers. Purpose: aerobic, motor planning, strengthening.

The fifth group of activities consists of cognitive tasks that are used in conjunction with activities from groups one through four and include the following: repeating phrases, singing lullabyes, ditties, and songs, counting forwards and backwards by multiples, giving directions to a location, recounting an actual event and creating a new story.

To summarize the combined activities, i.e. the combination of the auditory component with the visual/vestibular/movement component, of each of the four phases:

For organizational phase therapy the music and sounds selected are rich in lower frequency sounds and the music and sounds are treated to enhance the amplitude of lower frequency sound waves typically below 750 Hz in some of the music while also using the full spectrum of frequencies in the music. The visual and movement stimuli of the organizational phase therapy are simple exercises without any simultaneous combinations of visual, balance and cross-lateral activities.

For acclimation phase therapy the music and sounds are gradually filtered removing the lower frequency sound waves from 750 Hz to 3,000 Hz, including full spectrum music in which all frequencies are present. The visual and movement stimuli of the acclimation phase therapy begin to gradually blend visual, balance and cross-lateral activities.

For activation phase therapy the music and sounds are a series of increasingly filtered music where the maximal level of filtration is ~4,000Hz. The visual and movement stimuli of the activation phase therapy combine multi-sensory movement activities with simultaneous sequential and memory-based cognitive activities.

For integration phase therapy lower frequency sound waves that were filtered out in acclimation phase and activation phases are gradually reintroduced. The visual and movement stimuli combine more complex cognitive activities with simultaneous vestibular, proprioceptive, cross lateral, core strengthening and fine motor activities.

In addition to the sound wave frequency filtering of the described method, gating may also be employed. Gating alternately boosts the high and low frequencies in a random manner, activated by the amplitude of the recorded music and sounds. Gating occurs as an unexpected event and has the effect of heightening listening and attention by causing the brain to pay attention to an unexpected event.

The present disclosure also provides a flexible pad which can be used, for example, as a bed surface, crib mattress, fitted stroller pad, blanket, or pillow through which sound waves can be transmitted by bone conduction to an individual to be treated. One or more transducers are embedded within a flexible pad that, depending upon its overall size, may be applied to or wrapped around the individual to be treated. The pad can be constructed in size from a few inches square to any larger size. For example, the pad can be up to 6 feet in length enabling a person to lie completely on it and any a plurality of points of the muscular-skeletal system touch bone conduction transducers. The pad is applied to the individual so that its one or more transducers conduct sound waves to some part of the individual's skeletal frame such as the cranium, spine, hip, or leg bones. The pad allows the individual to be treated while sleeping, sitting, swinging on a swing, or performing other quiet type activities. The pad is also suitable for providing stimulation to a fetus in utero by placing the pad upon the mother's body. Additionally, the pad may be utilized to provide treatment of premature infants; in such an application, the pad serves as a bedding surface (e.g., crib mattress) with the head and/or body of the premature infant placed upon the area where a bone conduction transducer is located. Further, the pad may be sufficiently flexible and malleable to wrap around parts of the body, e.g., a user's feet or face. In at least one embodiment, the pad may take the form of an eye pillow with an adjustable clasp to ensure a proper fit around the user's head. In another embodiment, the pad may take the form of an adjustable headband. The one or more bone conduction transducers are utilized to provide sound wave bone conduction rich in low frequencies, primarily between 50 and 1,000 Hz.

The sound source to be transmitted through the one or more transducers is typically supplied by a tape player, CD player, or MP3 player. The sound selected for transmission may include full spectrum music, music rich in low frequencies, music filtered to remove higher frequency content, a recorded heartbeat and other rhythmic sounds which have a soothing and stabilizing effect. The pad may comprise an internal pocket where the sound source can be stored during use. In another embodiment, the pad may comprise a wireless receiver built into the pad so it can receive sound signals from a source outside the pad without connecting wires.

The flexible bone conduction pad comprises a cover, typically of waterproof textile fabric, which encloses the entire pad. Likewise, the pad itself may be made to be waterproof. One or more bone conduction transducers are located within a recess formed within a sheet of foam padding or textile batting to provide a comfortable transition surrounding the transducer. In at least one embodiment, a plurality of bone conduction transducers may be located in a pattern (e.g., a square matrix) based on typical pad usage that ensures that even with movement (conscious or unconscious) a user remains in contact with at least one bone conduction transducer. Electrical leads extend from the one or more transducers to a pocket at the periphery of the pad where an electrical connector is provided for connection to the sound source contained within the pocket. As the sound source, transducer and leads are all contained within the cover of the pad, an individual being treated cannot become entangled within the leads from the sound source to the transducer.

The flexible bone conduction pad may also comprise a heating element and associated controller to regulate the temperature of the pad. In one embodiment, the flexible bone conduction pad may comprise one or both of an accommodation space for aroma therapy products and one or more lights sources to provide light therapy to the user, which may or may not be synchronized to the sound source. In another embodiment, the flexible bone conduction pad may also comprise a canopy which may be located around the user's head to block outside light thereby creating a sensory-controller environment.

In an alternate embodiment of the foregoing disclosure additional filler material is utilized, in place of, or in addition to the sheet of foam padding or textile batting. The additional filler material is comprised of particles of firm material capable of transmission of low frequency sound waves in the range of 50 to 4,000 Hz. Although various shapes and materials may be employed, spherical glass beads of about ⅛ inch have been found to be well suited. The particles of firm material are distributed throughout a section of the pad and enclosed within a bag containing a transducer in at least a density that provides contact between adjacent particles and contact between a transducer and adjacent particles. The particles thereby provide a means of bone conduction adjacent to the location of a transducer and expand the sound conduction site over a larger area.

In yet another embodiment of the flexible bone conduction pad, the pad may comprise a plurality of ridges across the top surface to provide tactile sensory input to the user.

The bone conduction pad of the present disclosure has been found to have application of particular import in the treatment of infants and premature infants. In application the infant is placed upon the pad with its head and/or body located upon a transducer site. For example, the pad may take the form of a crib mattress or stroller pad. Sound that is rich in low frequencies, primarily between 50 and 1,000 Hz is selected, although the overall range of sound frequencies may be between 50 and 4,000 Hz. Classical music pieces such as Mozart, Bach, cello pieces and female Gregorian chants have been employed. Such pieces are filtered to remove higher frequency content that has an agitating effect upon infants and premature infants. Additionally, the sound is blended with a recorded heartbeat which provides rhythm and has a calming effect.

The foregoing embodiments of the present disclosure were developed to provide bone conduction delivery of sounds in the absence of air conduction; however, it should be recognized that the device could allow for a splitter to be employed at the music source to provide simultaneous air conduction with headphones or the like. Such simultaneous air conduction would allow combined air conduction and bone conduction stimulation for the individual to be treated or allow a mother to monitor the sounds conducted to her fetus in utero.

DETAILED DESCRIPTION OF THE DRAWINGS

Figure 1:
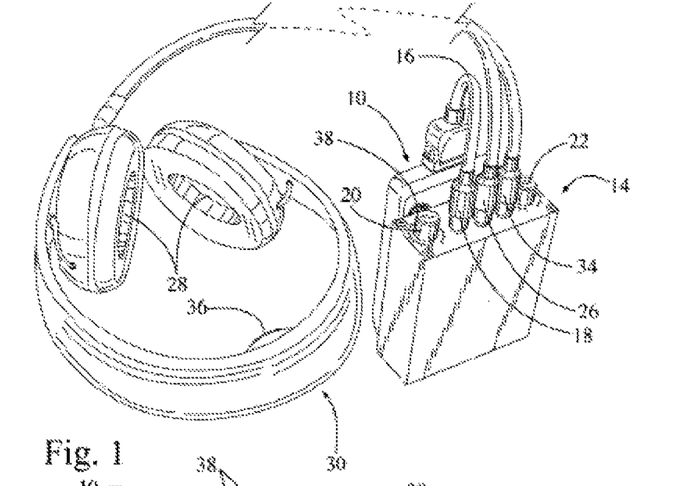
FIG. 1 is a perspective view of the recording playback device, amplifier and headphones having a bone conduction transducer that are utilized in the present disclosure.
Figure 2:
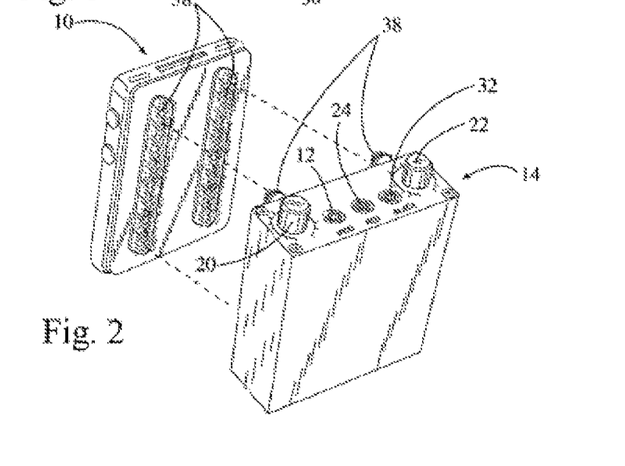
FIG. 2 is a perspective view of the recording playback device and amplifier that are utilized in the present disclosure.

Referring to FIGS. 1 and 2, an auditory stimulus is provided by filtering and treating recorded music and sounds as described in the description of the invention. The filtered and treated music and sounds are loaded onto a recording playback device 10, such as an i-Pod™ device.

The playback signal from the recording playback device 10, is provided to the multi-conductor input jack 12 of an amplifier 14, through a multi-conductor audio input cable 16 having a multi-conductor input plug 18. The amplifier 14 splits the playback signal into separate and distinct output signals, one for air conduction output and one for bone conduction output. The amplifier provides for separate adjustment of the amplitude of the air conduction output signal and the bone conduction output signal through air conduction amplitude adjustment 20 and bone conduction amplitude adjustment 22, respectively. The air conduction output signal from the amplifier 14 is transmitted through a multi conductor air conduction output jack 32 to a multi conductor air conduction output plug 34 that is connected to a pair of air conduction headphones 28 contained in a headphone assembly 30. The bone conduction output signal from the amplifier 14 is transmitted through multi conductor bone conduction output jack 24 to a multi conductor bone conduction output plug 26 that is connected to a bone conduction transducer 36 contained in a headphone assembly 30. The bone conduction transducer 36 is located within headphone assembly 30 so that when headphone assembly 30 is worn by a subject the bone conduction transducer 36 is in contact with the subject's skull.

The recording playback device 10, and the amplifier 14 are preferably attached to one another with removable adhesive material 38 to prevent them from banging together during movement activities, or may be integrated into one device. Additionally, securing the recording playback device 10 to the amplifier 14 allows them to be readily placed in the subject's pocket or secured in a waist pack worn by the subject during movement activities.

Figure 3:
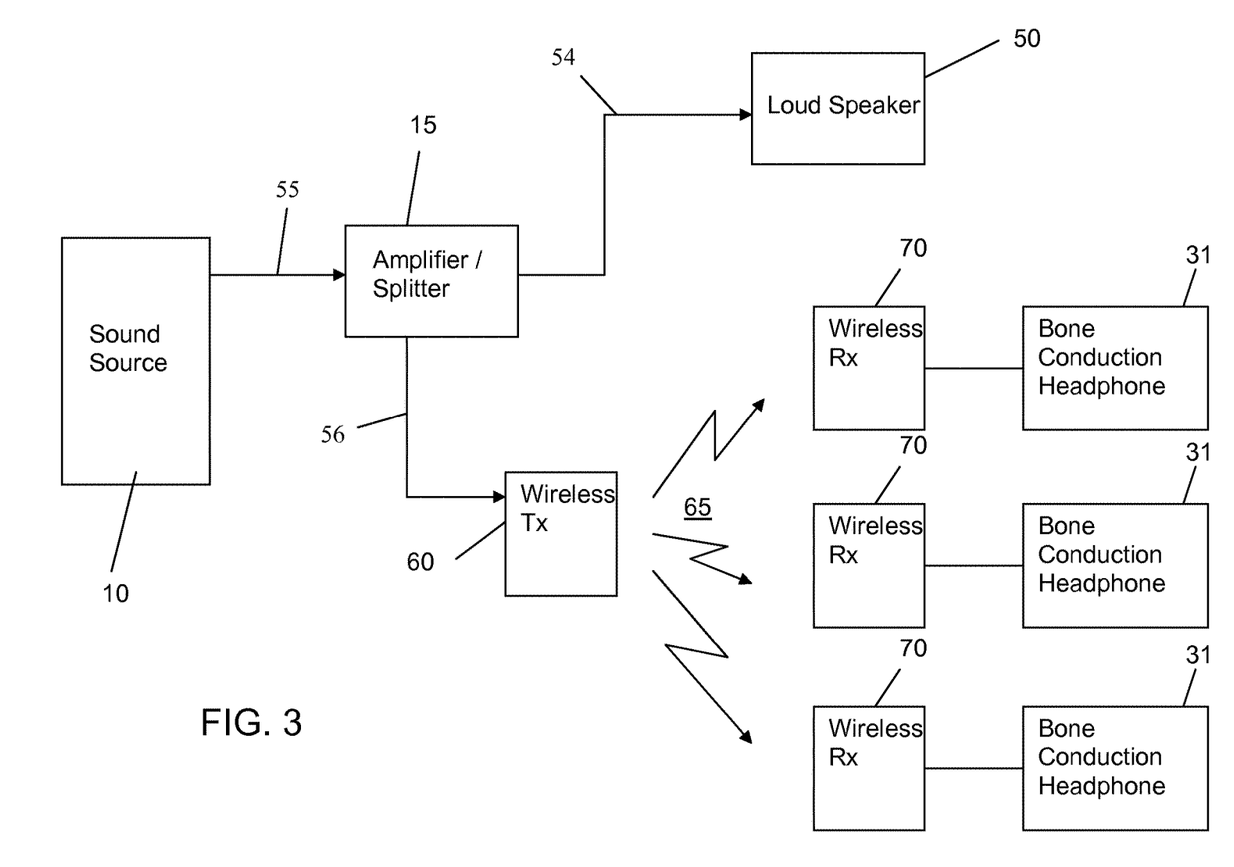
FIG. 3 is a schematic view of a group usage set-up comprising a plurality of bone conduction only head phones wirelessly coupled to a recording playback device.

Referring to FIG. 3, an auditory stimulus is provided by filtering and treating recorded music and sounds as described herein. The filtered and treated music and sounds are loaded onto a recording playback device 10, such as an i-Pod™ device. In this embodiment, a wireless connection 65 between the treated music stored on recording playback device 10 and a plurality of bone conduction only headphones 31 allow a group of individuals to share the same bone conduction signal in a group setting.

A playback signal 55 from the recording playback device 10 is provided to an input (not shown) of amplifier/splitter 15 where it is split into an air conduction output signal 54 which is connected to loud speaker 50 and a bone conduction output signal 56 which is connected to wireless transmitter 60. The amplifier 15 provides for adjustment of the amplitude of the air conduction output signal 54 which is connected to one or more room speakers 50. The air conduction output signal 54 can thus be broadcast for all users via the loud speaker 50, whether a user is wearing bone conduction devices or not.

The bone conduction output signal 56 is transmitted to a wireless transmitter 60 for transmission to associated wireless receivers 70. A wireless signal 65 is thus communicated from wireless transmitter 60 to a plurality of wireless receivers 70, one associated with each set of bone conduction headphones 31. Each wireless receiver 70 may comprise a separate amplifier to boost the signal strength for adjusting the volume of the bone conduction headphones 31. Bone conduction headphones 31 are similar to the headphone assembly 30 shown in FIG. 1 except they do not comprise the air conduction devices and associated ear surrounds 28. The bone conduction headphones 31 do comprise one or more of the bone conduction transducers 36.

The wireless receiver 70 may be integrated into the bone conduction headphones 31 or may be a separate device and coupled via wires to headphones 31. In either situation, the wireless receiver 70 associated with each set of bone conduction headphones 31 provides adjustable volume control (not shown).

Figure 4:
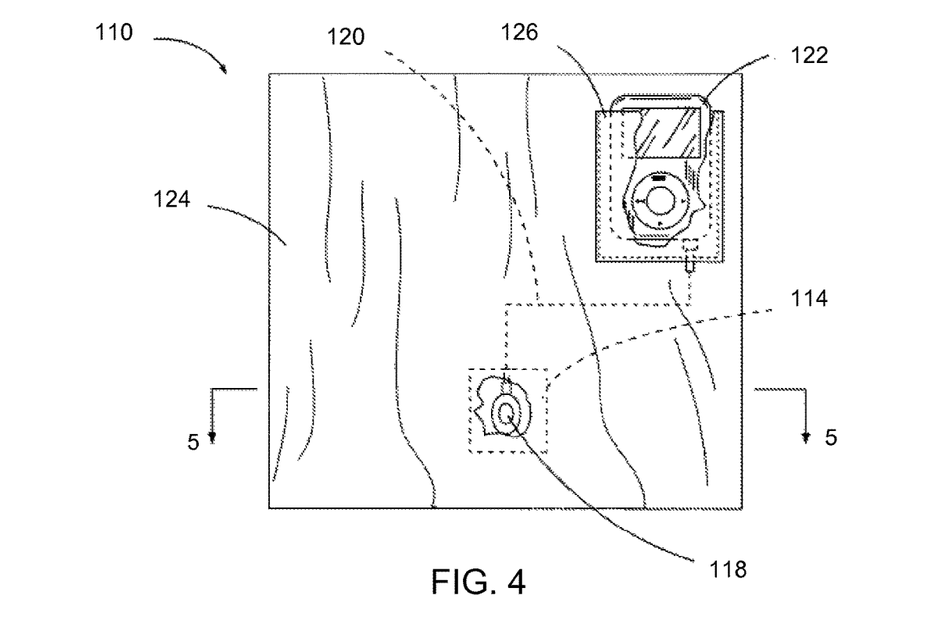
FIG. 4 is a plan view of a first embodiment of a bone conduction pad of the present disclosure.
Figure 5:
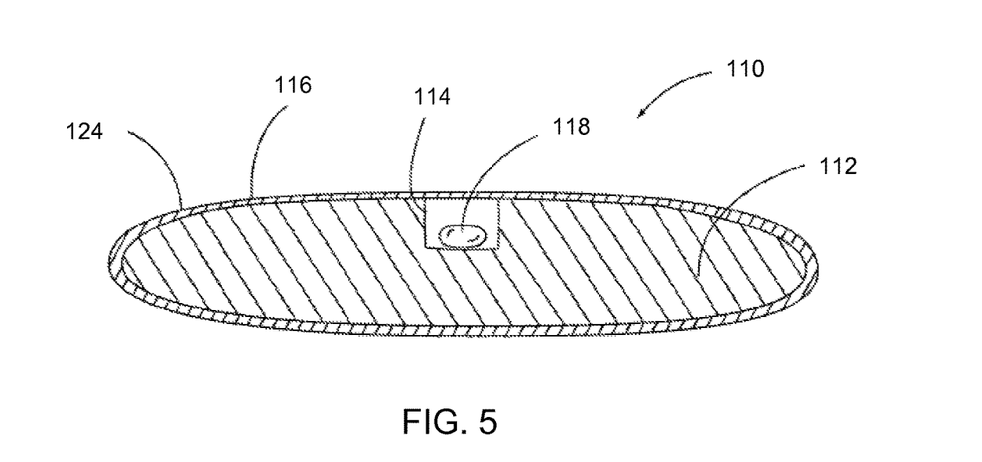
FIG. 5 a cross sectional view of a bone conduction pad of FIG. 4.
Figure 8:
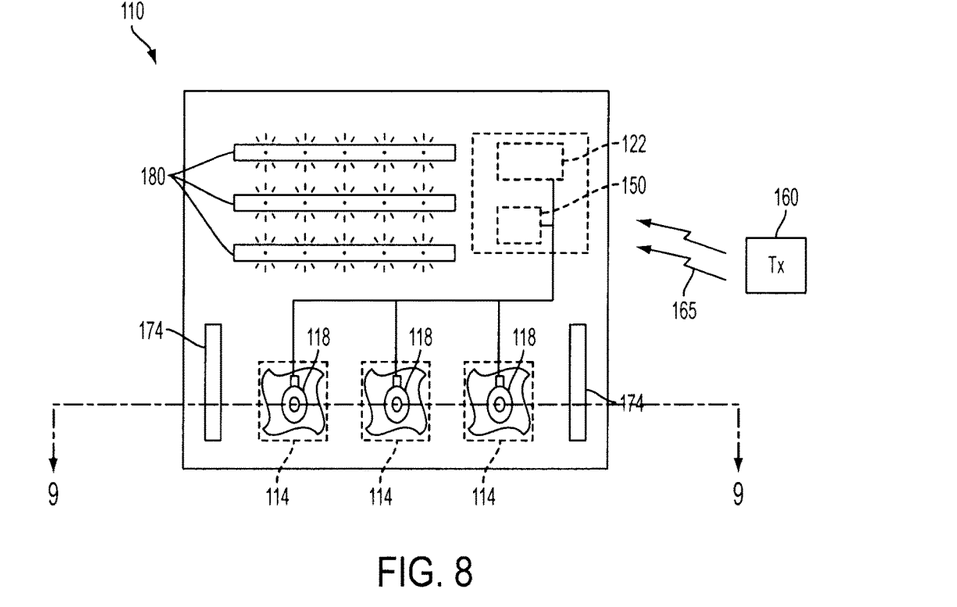
FIG. 8 is a plan view of a third embodiment of a bone conduction pad of the present disclosure.
Figure 9:
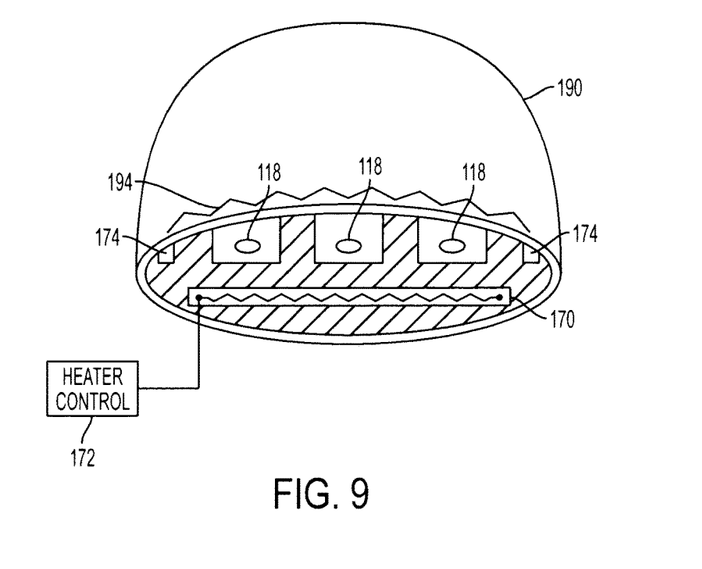
FIG. 9 a cross sectional view of the bone conduction pad of FIG. 8.

FIGS. 4 and 5 illustrate the bone conduction pad 110 of the present disclosure. Bone conduction pad 110 is constructed from a flexible sheet of padding 112 having a recess 114 formed in its upper face 116. The flexible sheet of padding 112 is typically made of foam or textile batting so that an individual being treated may comfortably lie upon or apply the bone conduction pad 110 to their body. The flexible sheet of padding 112 may be made waterproof. The flexible sheet of padding 112 may be 1 to 6 feet in length. The flexible sheet of padding 112 may also be flexible and malleable. Within recess 114 is located a bone conduction transducer 118. In one embodiment, shown in FIGS. 8 and 9, there are a plurality of recesses 114 strategically located on the flexible sheet of padding 112 based on typical usage. Bone conduction transducer 118 is particularly selected so that it is capable of emitting low frequency sound waves between 50 and 4,000 Hz. Bone conduction transducer 118 is electrically connected through electrical leads 120 to a sound source 122. In practice, the sound source 122 is typically a tape player CD player or MP3 player, however other devices capable of producing the appropriate low frequency sound signals may be employed. In one embodiment, the sound source 122 is a wireless receiver 150. A wireless transmitter 160 sends wireless sound source signals 165 from a location remote from the bone conduction pad 110. A cover 124 typically of waterproof textile material encloses the flexible sheet of padding 112, bone conduction transducer 118, electrical leads 120, and sound source 122. Cover 124 is constructed with a pocket 126 at its periphery to secure sound source 122. Flexible sheet of padding 112 may also be constructed with a pocket 126 at its surface to secure sound source 122.

In one application, the bone conduction pad 110 is positioned upon or under an individual so that bone conduction transducer 118 is able to emit low frequency waves to the skeletal frame of the individual. The signals provided to transducer 118 from sound source 122 are particularly selected, based upon the condition of the individual being treated, to provide sound waves that result in a particular therapeutic effect.

The flexible sheet of padding 112 may also comprise a heater 170 with a control 172 to regulate the temperature of the pad. In another embodiment, the flexible sheet of padding 112 may comprise locations for aroma therapy material 174 for depositing a plurality of fragrances and/or a plurality of light emitting devices 180 for light therapy.

In still another embodiment, the flexible sheet of padding 112 or cover 124 may comprise a canopy 190 to surround a user's head and provide a "sensory-controlled" environment, isolated from the surrounding environment. In another embodiment, the pad 112 has raised ridges 194 formed across its top surface to provide tactile sensory input.

Figure 10:
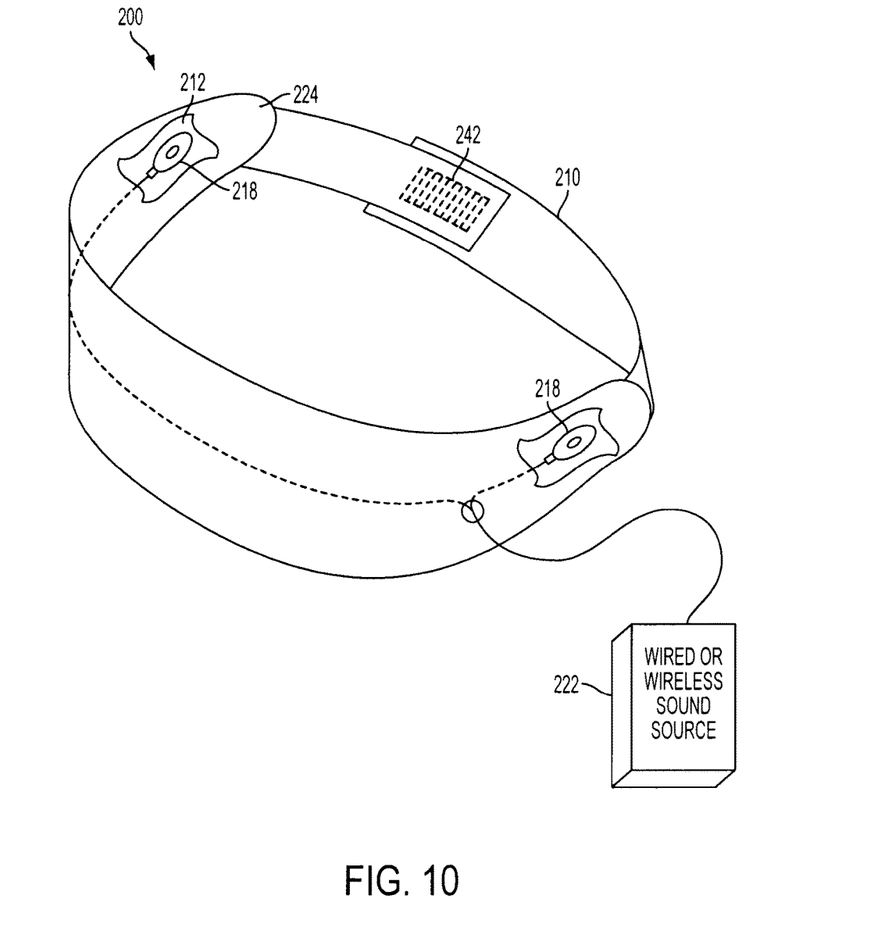
FIG. 10 is a perspective view of an eye mask employing the bone conduction pad principles disclosed herein.

In still another embodiment, shown in FIG. 10, the flexible sheet of padding 212 and/or cover 224 is formed in an eye mask configuration 200 with an adjustable head band 210 and at least a pair of bone conduction transducers 218 located on a surface of the pad such that when worn by a user, the transducers rest against the user's temples. In an alternative embodiment, one or more transducers 218 may be located at any location on the flexible sheet of padding 212. The adjustable head band 210 may comprise Velcro™ type attachments 242 or comprise elastic components. Other types of adjustment/connection mechanisms are also contemplated by this embodiment of the invention. The eye mask configuration 200 may be wired or wireless as previously discussed and may or may not have a sound source pocket for storage of a sound source 222. Such an embodiment may optionally comprise any of the other previously discussed features such as temperature control, aroma therapy, or light therapy.

Figure 11:
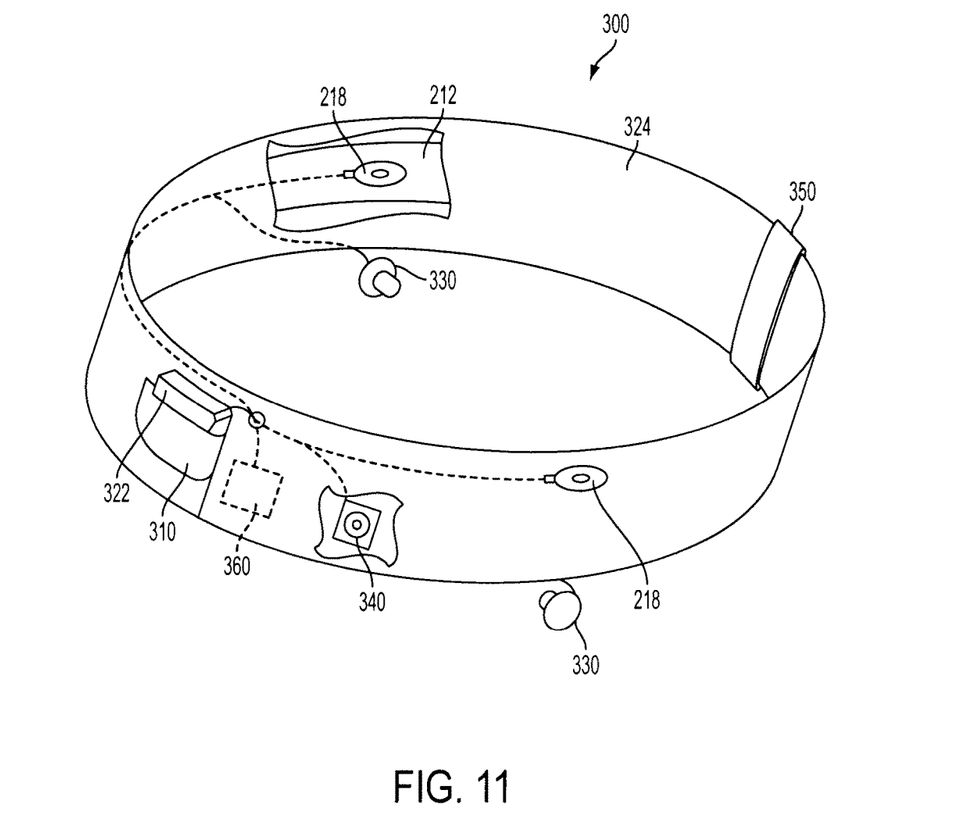
FIG. 11 is a perspective view of a headband employing the bone conduction pad principles disclosed herein.

In still another embodiment, shown in FIG. 11, the flexible sheet of padding 212 and/or cover 324 is formed in a headband configuration 300 with an optional adjustable clasp 350 or other tightening mechanism and one or more bone conduction transducers 218 located on a surface of the pad 212. The one or more transducers 218 may be located at any location on the flexible sheet of padding 212, and are preferably located such that when worn by a user, the transducer(s) 218 rest against the user's temples. The cover 324 may be made of a waterproof or non-waterproof material. The adjustable headband 300 may comprise elastic components, which along with the optional clasp 350 allow a user to properly adjust the headband. Other types of adjustment mechanisms are also contemplated by this embodiment of the invention. The headband configuration 300 may be wired or wireless as previously discussed and may or may not have a sound source pocket 310 for storage of a sound source 322. While the sound source pocket 310 is illustrated in the front of the headband, said sound source pocket 310 may be located at any location on the headband 300. One embodiment may optionally comprise any of the other previously discussed features such as temperature control, aroma therapy, or light therapy. In another embodiment, the headband 300 may further comprise air conduction speakers 330 in addition to the bone conduction transducers. While illustrated as ear bud type speakers, this embodiment of the invention contemplates any type of air conduction speaker. This embodiment also contemplates the air conduction speakers 330 being integrated into the cover 324 and/or the flexible sheet of padding 212. In yet another embodiment, the headband may comprise a Bluetooth or other wireless type receiver/transmitter 360 so that the sound source 322 does not have to be directly connected to the headband 300. In another embodiment, the headband likewise comprises one or more microphones 340 to pick up the user's voice, which in connection with the wireless type receiver/transmitter 360 could allow the headband to be used as a communication device, e.g., a headband telephone. The microphone(s) 340 might also be used to pick up ambient background noise, which can then be processed by a microprocessor (not shown) or electrical circuit (not shown) within the headband and outputted to the air conduction speakers 330 as a noise-canceling feature. While the headband 300 is not typically worn over a user's ear, it's structure is such that, at least in one embodiment, wearing over the user's ears allows the headband 300 to block outside noise and/or allow the user to listen to integrated air conduction speakers 330. While the headband 300 may be worn for a plurality of activities, such as exercising or outdoor activities, it is particularly contemplated that the headband 300 be used as a sleep or relaxation aid.

Figure 6:
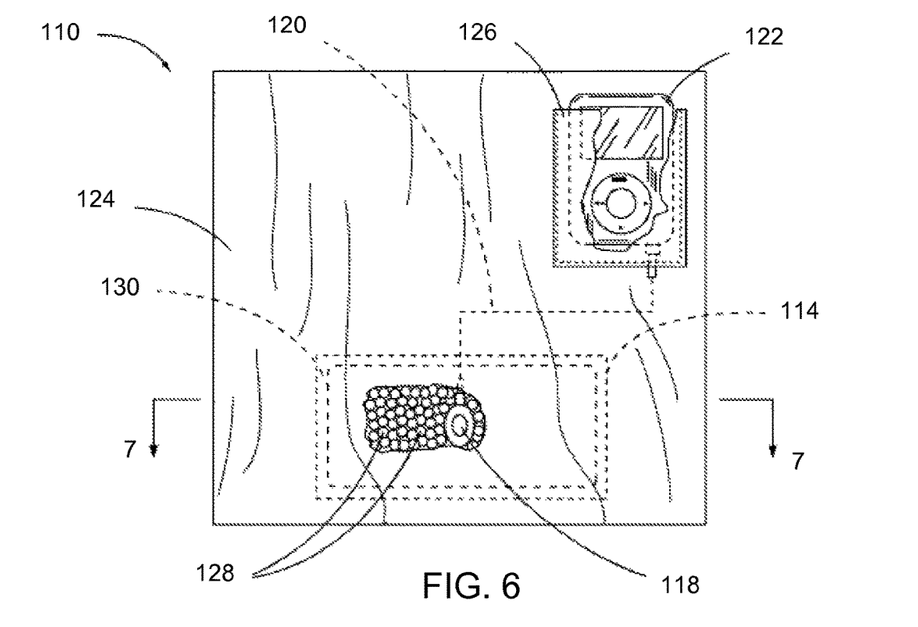
FIG. 6 is a plan view of a second embodiment of a bone conduction pad of the present disclosure.
Figure 7:
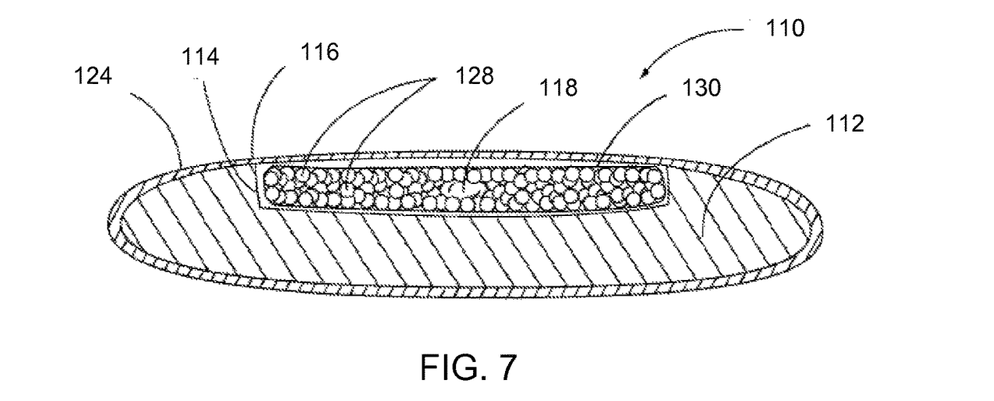
FIG. 7 is a cross sectional view of the alternate embodiment of the bone conduction pad of FIG. 6.

FIGS. 6 and 7 illustrate an alternate embodiment of the bone conduction pad 110 of the present disclosure. Bone conduction pad 110 of this alternate embodiment is constructed in the same fashion as the embodiment depicted in FIGS. 4 and 5, with the exception that transducer 118 is placed within and contacts a bed of particulate matter 128 that is enclosed within a flexible membrane 130. The recess 114 within the flexible sheet of padding 112 of this alternate embodiment is appropriately sized to accommodate transducer 118, and particulate matter 128.

In application of this alternate embodiment of the bone conduction pad 110, the area for bone conduction of low frequency waves between the bone conduction transducer 118 and the skeletal frame of the individual being treated is greatly increased. As the bed of particulate matter 128 surrounding the bone conduction transducer 118 transmits the waves emitted from the bone conduction transducer 118, the area of effective transmission is greatly increased; as a result, placement of the bone conduction pad 110 need not be as precise and remains effective despite activity that may unintentionally displace the bone conduction pad 110.

What is claimed is:

1. A method for the enhancement of sensory processing and sensory integration of a subject within a setting including a plurality of subjects, comprising:
   evaluating the subject to determine one or more deficiencies within one or more developmental phases;
   developing a therapeutic regimen to remedy the determined deficiencies;
   filtering a composition, comprising music and sounds, to change the relative amplitude of a frequency range within the composition and generating two output signals;
   delivering said filtered composition to the plurality of subjects through air conduction audio room speakers based on a first output signal of the two output signals;
   transmitting wirelessly, to combination air conduction/bone conduction headphones of the subject, a second output signal derived from said filtered composition; and
   directing said subject to perform one or more activities from one or more groups of activities associated with said frequency range, each activity directed toward the one or more determined deficiencies,
   wherein an amplitude of the first output signal and the second output signal are independently variable, and
   wherein the combination air conduction/bone conduction headphones include controls such that an amplitude of the second output signal driving the air conduction portion of the headphones and the second output signal driving the bone conduction portion of the headphones are independently variable.

2. The method of claim 1, wherein the frequency range is one of:
   (a) 0 -750 Hz,
   (b) 750 -3,000 Hz, and
   (c) greater than 3,000 Hz; and
   wherein the complexity of the one or more activities increases respectively from frequency range (a) to frequency range (c).

3. The method of claim 2, further comprising:
   gating the filtered composition.

4. The method of claim 3, wherein the one or more activities include autonomic nervous system exercises, balance and eye tracking exercises, language exercises, oculomotor exercises, and cognitive exercises.

5. The method of claim 1, wherein the developmental phases include an organization phase, an acclimation phase, and activation phase, and an integration phase.

6. The method of claim 1, wherein the groups of activities include:
   (a) breathing, balance, and core exercises;
   (b) visual motor activities involving beanbags and bouncing balls;
   (c) visual motor activities involving a hanging ball;
   (d) digital dexterity activities; and
   (e) cognitive tasks.

7. A system, comprising:
   an auditory system which includes:
      a sound source;
      an amplifier/splitter coupled to the sound source for amplifying a frequency range and splitting a playback signal provided by the sound source, the amplifier/splitter outputting a first output signal and a second output signal;
      one or more room speakers coupled to the amplifier/splitter for receiving and outputting the first output signal;
      a wireless transmitter coupled to the amplifier/splitter for transmitting the second output signal;
      one or more wireless receivers that receive the transmitted second output signal;
      one or more combination air conduction/bone conduction headphones each coupled to one wireless receiver and configured to output the second output signal,
      wherein an amplitude of the first output signal and the second output signal are independently variable, and
      wherein the combination air conduction/bone conduction headphones include controls such that an amplitude of the second output signal driving the air conduction portion of the headphones and the second output signal driving the bone conduction portion of the headphones are independently variable; and
   therapy equipment which includes:
      a balance board;
      a hanging ball;
      a balancing ball; and
      a bean bag,
   wherein the therapy equipment is used with the auditory system to improve motor function, sensory processing, and cognitive development.

* * * * *